United States Patent
Beijnen et al.

(10) Patent No.: US 11,571,408 B2
(45) Date of Patent: *Feb. 7, 2023

(54) CANCER TREATMENT USING DOCETAXEL BY CONTROLLING PEAK PLASMA LEVELS

(71) Applicant: Modra Pharmaceuticals B.V., HN Amsterdam (NL)

(72) Inventors: Jacob Hendrik Beijnen, HN Amsterdam (NL); Johannes Henricus Schellens, HN Amsterdam (NL)

(73) Assignee: MODRA PHARMACEUTICALS B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/833,745

(22) Filed: Jun. 6, 2022

(65) Prior Publication Data

US 2022/0323399 A1   Oct. 13, 2022

Related U.S. Application Data

(63) Continuation of application No. 17/416,977, filed as application No. PCT/EP2019/086124 on Dec. 18, 2019.

(30) Foreign Application Priority Data

Dec. 21, 2018   (EP) ..................... 18215472

(51) Int. Cl.
*A61K 31/337* (2006.01)
*A61P 35/00* (2006.01)
*A61K 31/426* (2006.01)

(52) U.S. Cl.
CPC .......... *A61K 31/337* (2013.01); *A61K 31/426* (2013.01); *A61P 35/00* (2018.01)

(58) Field of Classification Search
None
See application file for complete search history.

(56) References Cited

FOREIGN PATENT DOCUMENTS

| JP | 2010536837 A | 12/2010 |
| RU | 2429837 C2 | 9/2011 |
| WO | 2009027644 A2 | 3/2009 |
| WO | 2009027644 A2 | 5/2009 |
| WO | 2010020799 A2 | 2/2010 |

OTHER PUBLICATIONS

Japanese Office Action dated Jun. 28, 2022, issued in Japanese Patent No. 2021-536396, filed Jun. 21, 2022.
Japanese Office Action dated Jun. 28, 2022, issued in Japanese Patent No. 2021-536409, filed Jun. 21, 2022.
J J Ma Hendrikx et al: "Oral co-administration of elacridar and ritonavir enhaces plasma levels of oral paclitaxel and docetaxel without affecting relative brain accumulation", British Journal of Cancer, vol. 110, No. 11, Apr. 29, 2014 pp. 2669-2676.
Moes, J.J., et al., "Pharmacokinetic evaluation of three oral formulations of docetaxel boosted with ritonavir: two 2 single-drug formulations vs. a fixed-dose combination tablet," Drug Delivery and Translational Research, vol. 3, No. 3, Jun. 2013, pp. 243-251.
De Weger, V. A., Stuurman, F. E., Hendrikx, J. J. M. A., Moes, J. J., Sawicki, E., Huitema, A. D. R., . . . Marchetti, S. (2017). A Dose-Escalation Study of Bi-Daily Once Weekly Oral Docetaxel Either as ModraDoc001 or ModraDoc006 combined with ritonavir. European Journal of Cancer, 86, 217-225. doi: Publication Date Sep. 14, 2017, p. 220, Table 1; p. 222, point 3.7; pp. 222-224.
HIV-1 Protease Inhibitor, Ritonavir: A Potent Inhibitor of CYP3A4, Enhanced the Anticancer Effects of Docetaxel in Androgen-Independent Prostate Cancer Cells In Vitro and In Vivo Takayuki Ikezoe et al; Cancer Res . Oct. 15, 2004;64(20):7426-31. doi: 10.1158/0008-5472.CAN-03-2677, Publication Date Oct. 15, 2004, abstract, p. 7430.
Coadministration of Ritonavir Strongly Enhances the Apparent Oral Bioavailability of Docetaxel in Patients with Solid Tumors Roos L. Oostendorp et al; Clin Cancer Res 2009;15(12) Publication Date Jun. 15, 2009, abstract, table-2.
ModraDoc006/r in Metastatic Castration-Resistant Prostate Cancer: NCT03136640; URL:https://clinicaltrials.gov/ct2/history/NCT03136640? A=3&B=3&C=merged, Publication Date Apr. 27, 2017, p. 3.
Oostendorp R.L. et al. Coadministration of Ritonavir Strongly Enhances the Apparent Oral Bioavailability of Docetaxel in Patients with Solid Tumors / Clin Cancer Res, 2009; 15(12), pp. 4228-4233.
МИШУГИН С.В. и др Вторая линия химиотерапии при кастрационно-резистентном раке предстательной железы / Онкология. Журнал им. П.А. Герцена, 2014, 6, стр. 37-40.
Anonymous: "ModraDoc006/r in metastatic Castration-resistant prostate CAncer: NCT03136640", Jan. 26, 2018.
ModraDoc0006/r in Metastatic Castration-Resistant Prostate Cancer: NCT03136640, Jan. 26, 2019.
RU Office Action dated Apr. 29, 2022, issued in Serial No. 2021117553/14(037026) filed Dec. 18, 2019.

*Primary Examiner* — Brian J Davis
(74) *Attorney, Agent, or Firm* — Workman Nydegger

(57) ABSTRACT

Treatments of cancers involve a wide range of treatment. The current invention relates to chemotherapy of tumors using taxanes, in particular docetaxel. More in particular it relates to a method for the treatment of a cancer in a patient comprising orally administering an effective dose of docetaxel, whereby side effects are controlled by preventing peak plasma levels of docetaxel that induce said side effects, whilst maintaining an effective plasma level of docetaxel to eradicate tumor cells.

13 Claims, 12 Drawing Sheets

CANCER TREATMENT USING DOCETAXEL BY CONTROLLING PEAK PLASMA LEVELS

CROSS-REFERENCE TO RELATED APPLICATIONS

This application is a continuation of U.S. application Ser. No. 17/416,977, entitled EXTENDED USE OF DOCETAXEL IN THE TREATMENT OF CANCER, which entered the U.S. National Phase on Jun. 21, 2021 and is a nationalization of PCT/EP2019/086124, filed Dec. 18, 2019, which claims the benefit of and priority to European Application No. EP 18215472.4, filed Dec. 21, 2018, the entirety of each of the foregoing being incorporated herein by specific reference.

BACKGROUND OF THE INVENTION

Field of the Invention

The invention relates to chemotherapy of tumors using taxanes, in particular docetaxel. More in particular it relates to achieving efficacious doses of orally administered doses docetaxel whilst controlling sided effects allowing for an extended use.

Background

Treatments of cancers involve a wide range of treatment. Treatments include i.a., surgery, radiation therapy, chemotherapy, immunotherapy and cell therapy. Often, cancer treatments include a combination of different modes of treatments, comprising combinations of different therapeutic agents. As part of first line chemotherapy, docetaxel, a taxane, is used widely in the treatment of various cancers. Docetaxel is a cytotoxic agent, its main mode of action is understood to involve interference with microtubule assembly and disassembly, resulting in inhibiting mitotic cell division. The recommended dosage is a three-weekly intravenous administration, with a dose in the range of 75-100 mg/m2 of body surface area. Docetaxel is used in the treatment of a variety of cancers, which include breast, lung, prostate, gastric, head and neck, and ovarian cancer. While having the potential to benefit patients, improving life expectancy and quality of life, the use of docetaxel comes along with significant side effects. Typical side effects include i.a., neutropenia, a high risk of infections, thrombocytenia, anemia, alopecia, fluid retention, diarrhoea, nail toxicity, peripheral sensory neurotoxicity and infusion related reactions. Hence, the recommended mode of use involves a restricted number of cycles, usually 4-6 cycles, of docetaxel. In addition, standard premedication with high dose dexamethasone is needed every cycle.

SUMMARY OF THE INVENTION

Surprisingly it was found that when using oral administration of docetaxel, an effective treatment could be obtained having less of the side effects as observed with intravenous administration. Because of the use of oral administration, high peak concentrations of docetaxel as measured in plasma (which can also be measured in serum, or whole blood) can be avoided thereby allowing for extended periods of administrations. High peak concentrations of docetaxel in the blood are associated with most of the side effects as observed with intravenous administrations. When using oral administration and administering in a more frequent schedule, ranging e.g., from daily to weekly, instead of every three weeks as in standard licensed treatments of intravenous administrations of docetaxel, peak concentrations can be reduced even further, while maintaining a concentration of docetaxel in plasma that allows to effectively control cancer in a patient. Accordingly, the current invention provides for a method for the treatment of a cancer in a patient comprising orally administering an effective dose of docetaxel, whereby side effects are controlled by preventing peak plasma levels of docetaxel that induce said side effects, whilst maintaining an effective plasma level of docetaxel to eradicate tumor cells. The current invention also provides for a method for reducing side effects of the treatment of a cancer in a patient, wherein said method comprises the administration of docetaxel, wherein said docetaxel is administered orally, controlling side effects by preventing peak plasma levels of docetaxel that induce said side effects, whilst maintaining an effective plasma level of docetaxel to eradicate tumor cells. Reducing side effects and controlling side effects is of importance in general when using docetaxel. Moreover, reducing or controlling side effects now allows for an extended use of docetaxel. This may be of importance for combination therapies, in which combinations of anticancer treatments are combined e.g., to durably maintain control of a cancer for extended periods. Furthermore, the combined use of orally administered docetaxel with the use of a CYP3A inhibitor, such as ritonavir, provides for a further means allowing to maintain effective plasma levels of docetaxel to eradicate tumor cells while controlling or reducing side effects associated with the use of docetaxel.

BRIEF DESCRIPTION OF THE FIGURES

In FIG. 4 a plot is shown presenting AUC (average AUCs in h*ng/mL by dose level) of ritonavir (RTV) to ModraDoc006 (docetaxel). It shows that exposure of Modrodoc006 appears to be highly correlated to overall Ritonavir AUC (and dose).

In FIG. 5A a plot is shown indicating similar or moderately higher levels of docetaxel AUC are obtained in patients with ModraDoc006/r as compared with IV.

The target minimum AUC threshold in mCRPC patients is highlighted and ranges from about 600-800 h*ng/mL. This represents, at its lower limit, the weekly AUC of IV docetaxel in mCRPC patients (1820/3=±600 h*ng/mL [dividing q3w AUC of 1820 by 3 to yield weekly equivalent]. Source: De Vries Schultink et al, "Neutropenia and docetaxel exposure in metastatic castration-resistant prostate cancer patients: A meta-analysis and evaluation of a clinical cohort", Cancer Medicine, February 2019. At its upper limit, this represents 1418*55%=±800 h*ngXX/ML —where 1418 represents the AUC of ModraDoc006/r in its phase I study N10BOM. 55% (1820/3300) represents the ratio of AUCs for IV docetaxel in mCPRC patients vs other tumors (De Vries Schultink et al, "Neutropenia and docetaxel exposure in metastatic castration-resistant prostate cancer patients: A meta-analysis and evaluation of a clinical cohort", Cancer Medicine, February 2019).

Figure 5A:
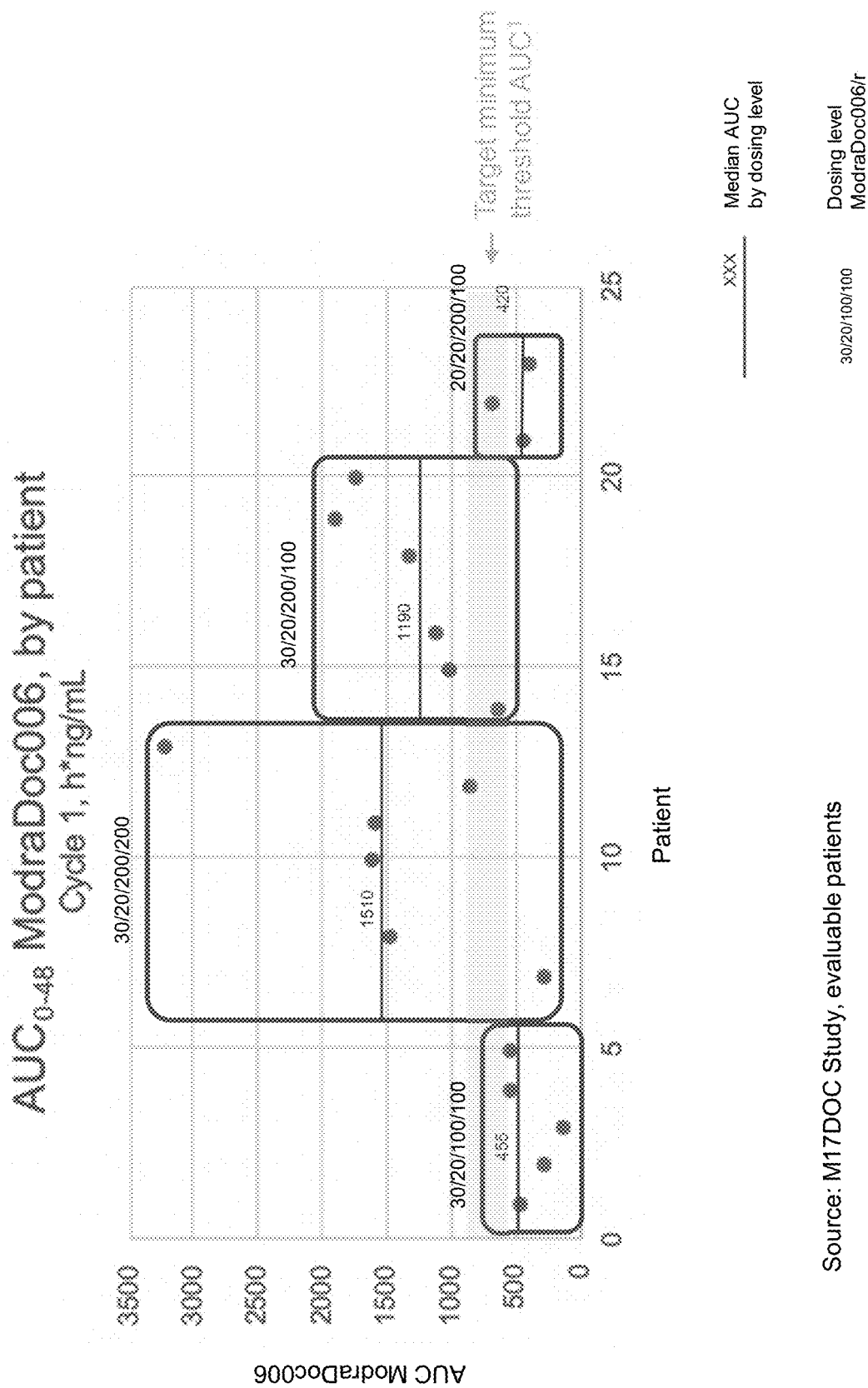
Figure 5B:
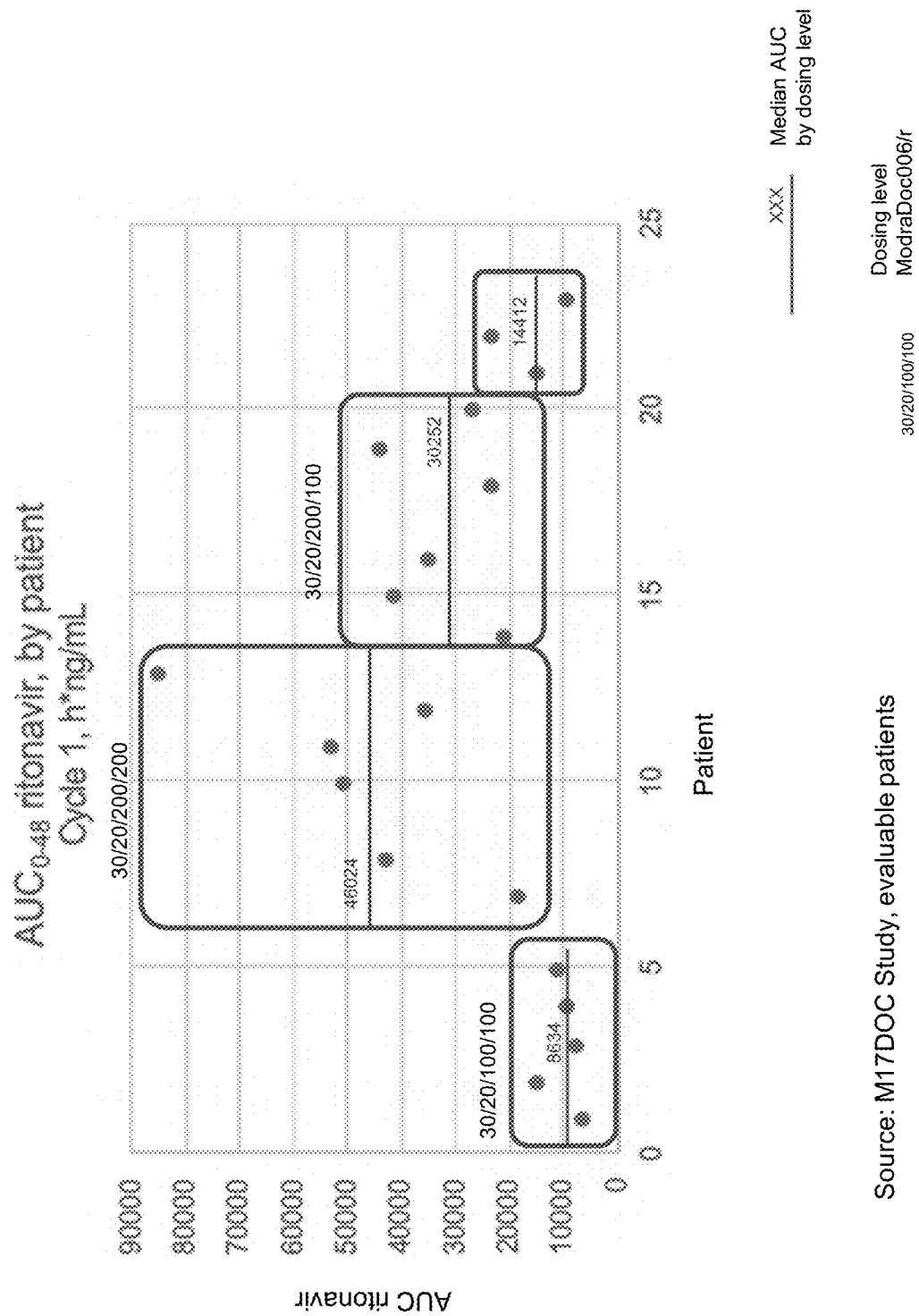

In FIG. 5B a plot is shown with the AUC of ritonavir.

Figure 6:
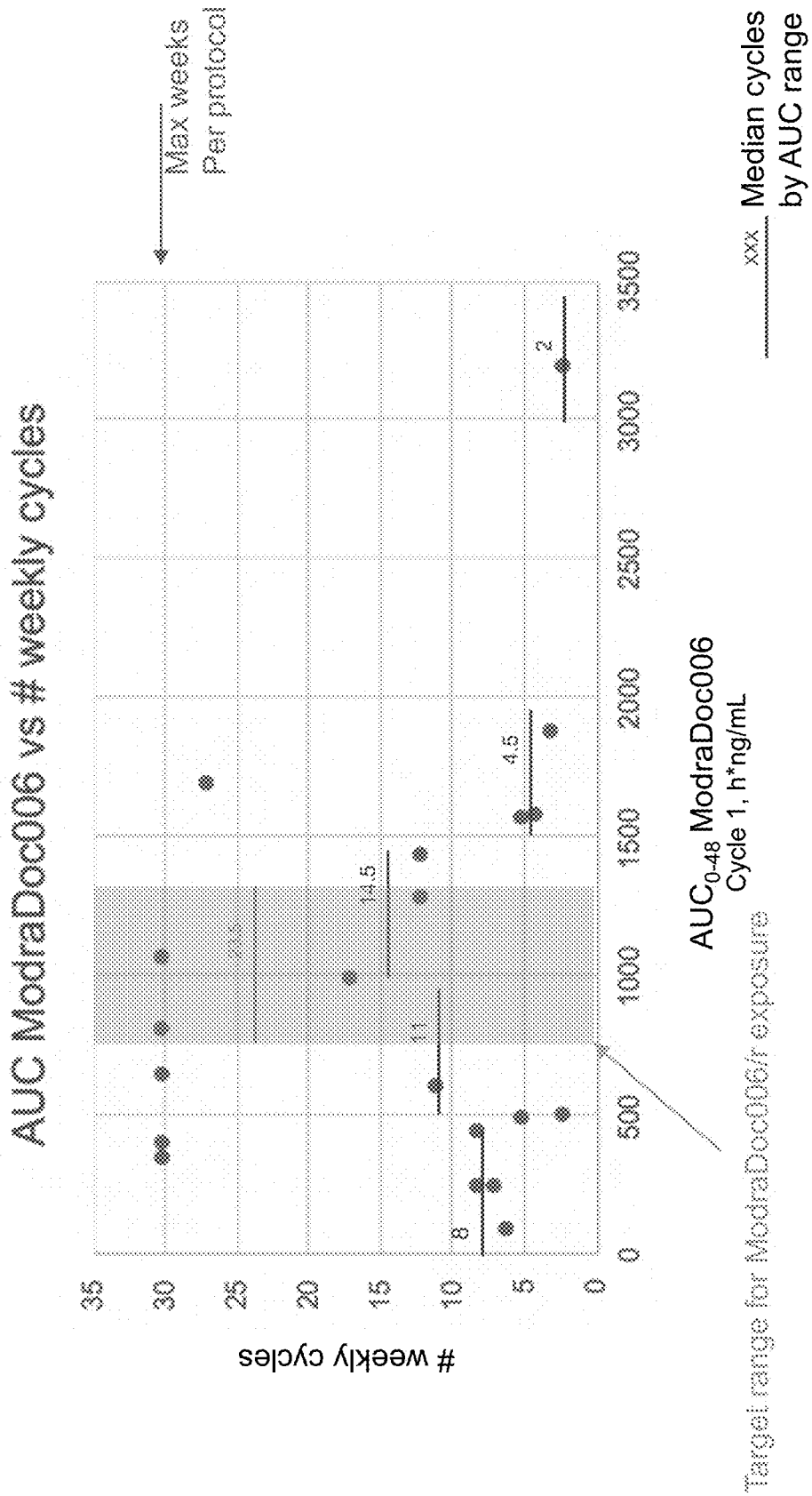

In FIG. 6 a plot is shown of docetaxel AUC and number of cycles. Length of treatment appears to be trending longer in patients in a target docetaxel range between 500-1500 h*ng/mL.

Figure 7:
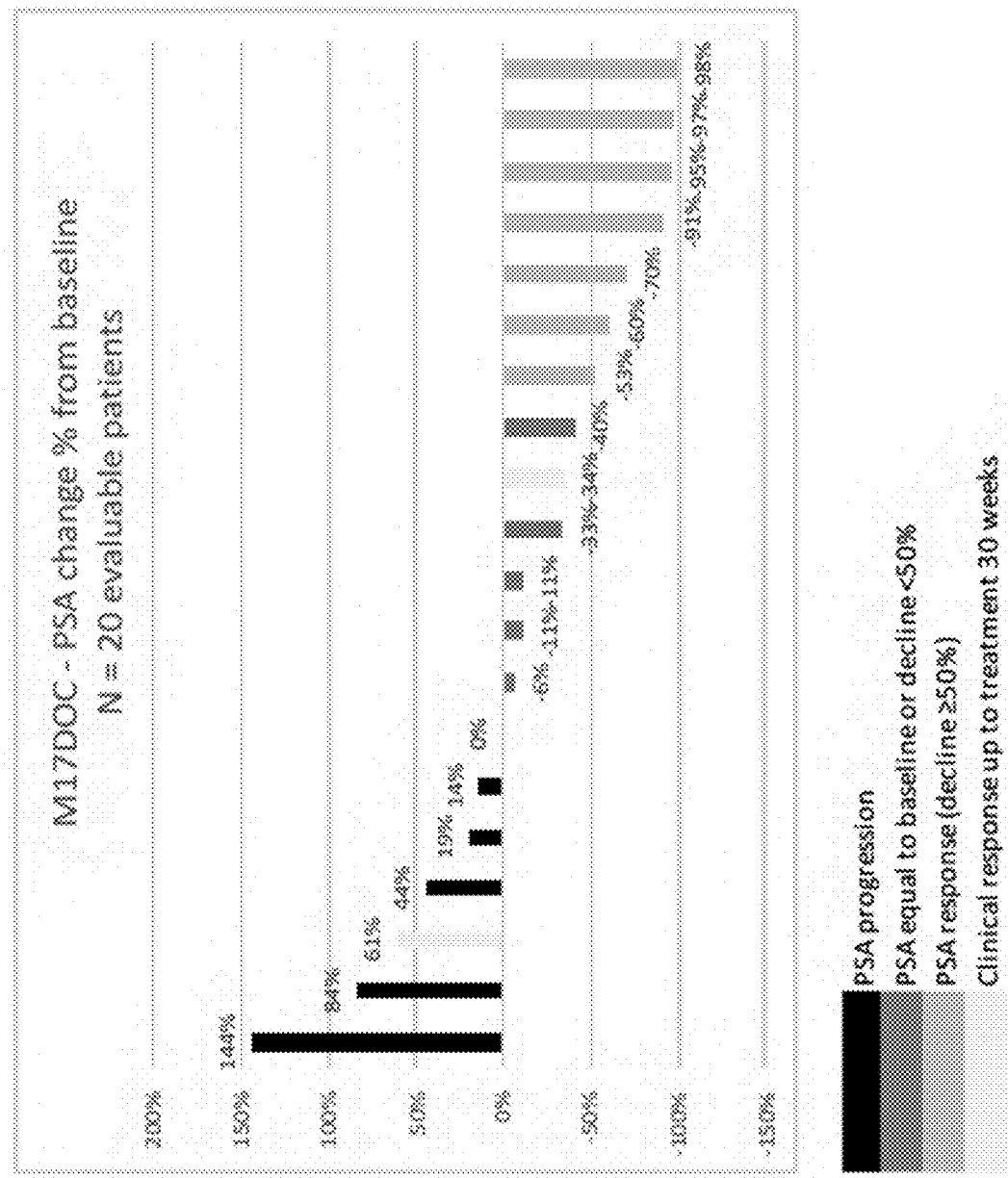

In FIG. 7 a plot is shown of PSA (prostate specific antigen) change % from baseline in a multicenter clinical phase IB study in mCRPC (M17DOC) of evaluable patients. Patients were scored as PSA progression (black bars); PSA equal to baseline or decline (<50%) (dark grey bars); PSA response (decline ≥50%) (medium grey bars); clinical response (pain reduction) up to the maximum treatment period permitted in the protocol of 30 weeks (light grey bars).

Figure 8:
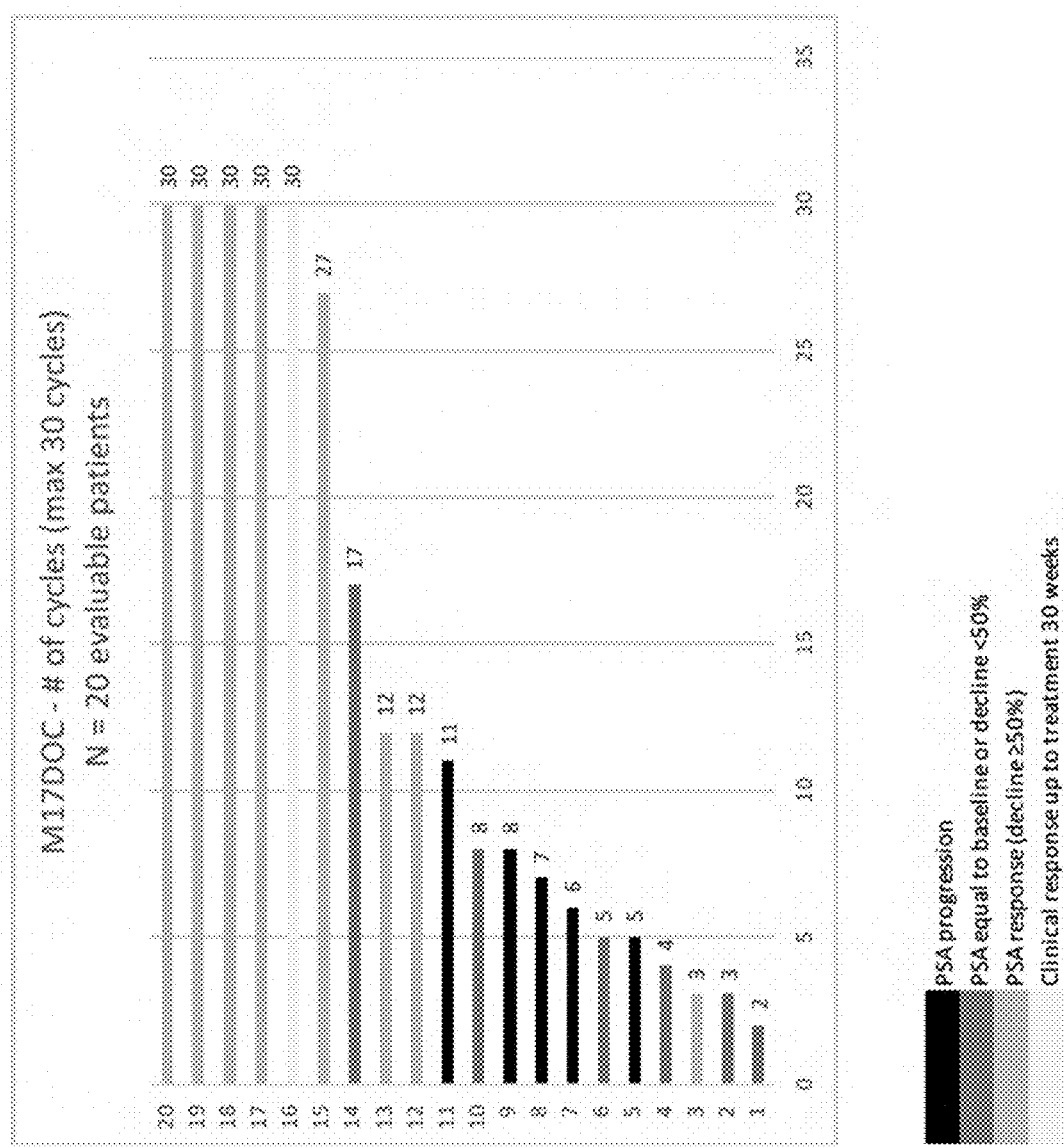

In FIG. 8 a plot is shown of the number of treatment cycles (with a maximum of 30) in a multicenter clinical phase IB study in mCRPC (M17DOC) of evaluable patients. Patients were scored, as PSA progression (black bars); PSA equal to baseline or decline (<50%) (dark grey bars); PSA response (decline ≥50%) (medium grey bars); clinical response (pain reduction) up to the maximum treatment period permitted in the protocol of 30 weeks (light grey bars).

Figure 9:
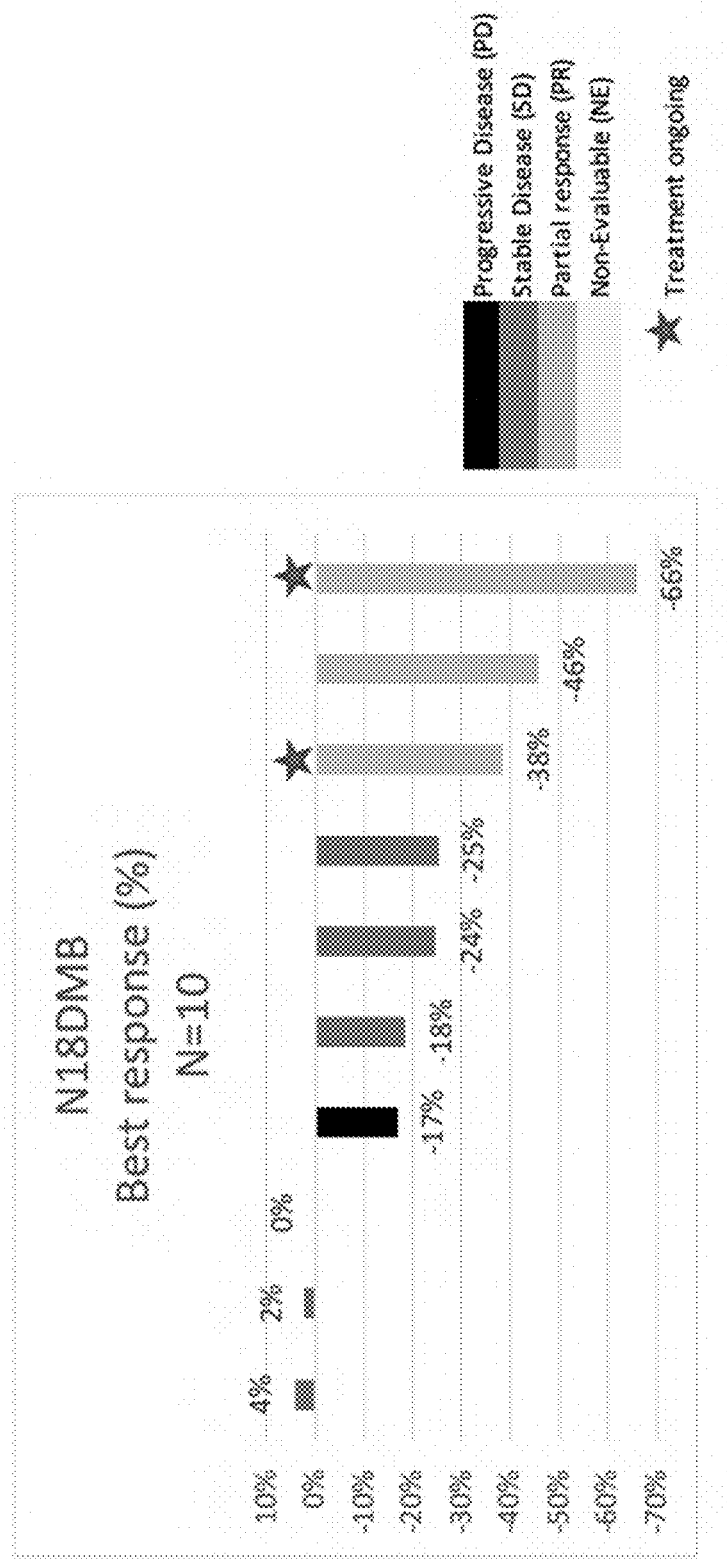

In FIG. 9 a plot is shown of best responders in a multicenter phase IIA study in HER2-metastatic breast cancer (mBC) (N18DMB) of 10 patients evaluable for response with regard to tumor measurements, a negative % indicating the percentage decrease of tumor size. Patients were scored as having progression disease (PD) (black bars); Stable disease (SD) (dark grey bars); partial response (PR) (medium grey bars); or non evaluable (NE) (light grey bars). Patients indicated with a star have treatment ongoing.

Figure 10:
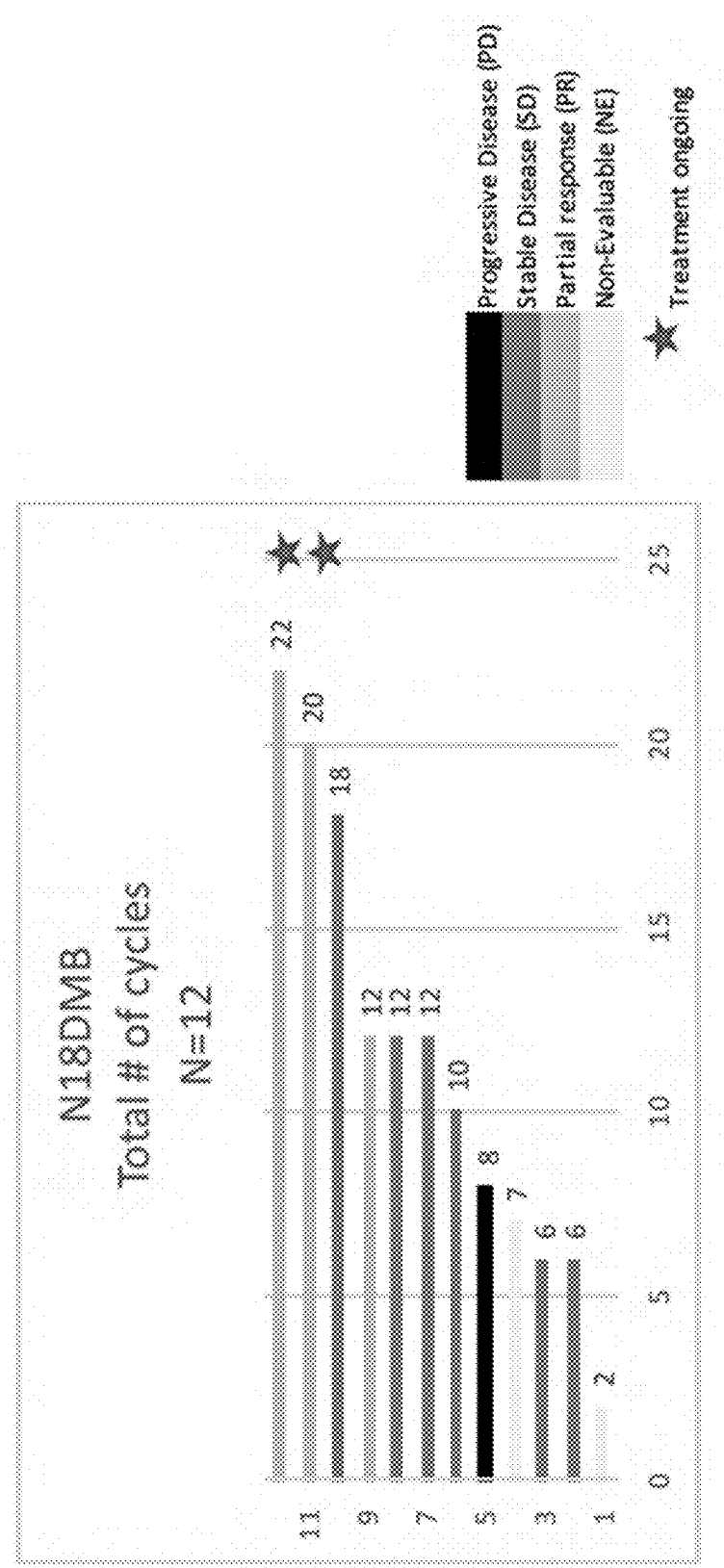

In FIG. 10 a plot is shown of the total number of cycles in in a multicenter phase IIA study in HER2- metastatic breast cancer (mBC) (N18DMB) of 12 patients evaluable for safety evaluation. Patients scores were also indicated as having progression disease (PD) (black bars); Stable disease (SD) (dark grey bars); partial response (PR) (medium grey bars); or non evaluable (NE) (light grey bars). Patients indicated with a star have treatment ongoing.

DETAILED DESCRIPTION

The present invention provides for a method for the treatment of a cancer in a patient comprising orally administering an effective dose of docetaxel, whereby side effects are controlled by preventing peak plasma levels of docetaxel that induce said side effects, whilst maintaining an effective plasma level of docetaxel to eradicate tumor cells. The standard route of administration of docetaxel currently in use in the clinic involves intravenous administration of docetaxel. As the intravenous administration is directly in the blood stream, this route of administration results in a high peak concentration of docetaxel as measured in the blood plasma or serum. However, while high peak plasma levels may induce side effects, high peak plasma levels may contribute to the cytotoxic effect of docetaxel on cancer cells, and thus contribute to therapy. Surprisingly, however, the inventors have found that for effective treatment of a cancer in a patient, it is of importance to maintain effective plasma levels and to avoid peak plasma levels. By using an alternative route of administration, oral administration, such high peak plasma levels may be largely avoided. Hence, side effects of the treatment of a cancer in a patient can be reduced. The present invention also provides for a method for reducing side effects of the treatment of a cancer in a patient, wherein said method comprises the administration of docetaxel, wherein said docetaxel is administered orally, controlling i.a., side effects by preventing peak plasma levels of docetaxel that induce said side effects, whilst maintaining an effective plasma level of docetaxel to eradicate tumor cells.

As used herein, peak plasma levels are defined as the maximum concentration of a compound that can be measured in blood plasma obtained from a patient after administration of a pharmaceutical composition. Usually, peak plasma levels can be measured shortly after administration, but depending on the route of administration and the composition of the pharmaceutical composition there may be a lag between the time of administration and peak plasma levels measured. In intravenous administration of docetaxel, the peak level can be measured e.g., at the end of the infusion. In oral administration of docetaxel, the time point at which the peak level occurs after oral administration may vary. The peak level may occur about 2-12 hours, e.g., 4 hours, after an oral administration.

Plasma levels of docetaxel can be measured by methods know in the art (Hendrikx et al. J. Chrom. B, 2011), which may include liquid chromatography and mass spectrometry methods, such as e.g., described in the examples. Plasma is a blood component, it is understood that instead of measuring docetaxel in blood plasma, one can also determine levels of docetaxel in whole blood or in serum. Measurements of docetaxel, e.g., peak levels and area under the plasma concentration-time curve, in short area under the curve (AUC), herein are defined relative to (blood) plasma but can easily be recalculated to corresponding peak levels in whole blood or serum. In any case, high peak plasma levels that are to be avoided can be defined as docetaxel peak plasma levels of 3000 ng/mL or higher. Preferably, the docetaxel peak plasma level in oral administration is at most 2500 ng/mL, preferably at most 2000 ng/mL, more preferably at most 1500 ng/mL most preferably the peak plasma level in oral administration is at most 1000 or even 500 ng/mL.

As used herein, the phrases "effective plasma level" means a plasma concentration as measured in a subject that provides the specific pharmacological effect of docetaxel in a subject, i.e., eradicating cancer cells. An effective plasma level herein is defined as an area under the curve (AUC) as determined in the first 48 hours after the administration of docetaxel, wherein the AUC is within the range of 250-2500 ng·h/mL. Preferably the AUC is in the range of 750-2500 ngh/mL. Preferably, the AUC is at least 400 ngh/mL, at least 500 ngh/mL, more preferably at least 600 ngh/mL, at least 1000 ngh/mL, more preferably at least 1200 ngh/mL. Preferably, the AUC is at most 2500 ngh/mL, more preferably at most 2250 ngh/mL, more preferably at most 2000 ngh/mL, at most 1800 ngh/mL, at most 1700 ngh/mL, more preferably at most 1500 ngh/mL. The AUC may more preferably be within the range of 800-1400 ngh/mL. The area under the curve (AUC; ngh/mL) is determined in the first 48 hours after the administration of docetaxel, during which the docetaxel concentration in blood plasma can be measured at several timepoints, and the surface of the area under the curve can be calculated from the plotted values. Herein, plasma concentration-time curve, area under the curve, or AUC, with reference to docetaxel are used interchangeably and refer to the area under the curve in the first 48 hours (ngh/mL) after the administration of docetaxel.

Eradicating cancer cells is understood to comprise the killing of cancer cells such that e.g., in case of a solid tumor, the growth of the solid tumor is reduced as compared with the growth of a tumor not having an effective plasma level of docetaxel present. The growth of a tumor may be reduced to such an extent that a tumor may be eradicated as well. It is emphasized that an effective plasma level may not always be effective in treating the conditions described herein in all subjects, even though such is deemed to be therapeutically effective by those of skill in the art.

Side effects that may be controlled or reduced in the current treatment include neutropenia. Neutropenia is an abnormally low concentration of neutrophils in the blood. Neutropenia is usually diagnosed by determining the absolute neutrophil count in the blood. As a reference, a healthy range of neutrophil count in the blood can be defined as having 1500-4000 cells per microliter of blood. Neutropenia may be diagnosed when the level of neutrophils is below 1500 cells per microliter of blood. Assays to determine neutrophil counts are widely available as part of e.g., a complete blood count analysis as part of routine laboratory testing. Accordingly, in the current invention, the incidence of neutropenia is significantly reduced in the patient population while concomitantly providing for an effective treatment of the cancer in patients. Hence, preferably, in the method of treatment of a cancer in a patient, the side effect neutropenia is controlled or reduced. Other side effects that may be controlled or reduced are thrombocytopenia, neuropathy, alopecia, fluid retention, neurotoxicity, and/or nail toxicity.

Further side effects that may be avoided by using oral administration of docetaxel include infusion-related reactions due to e.g., excipients (i.a., Tween-80, ethanol) used in intravenous formulations of docetaxel. Corticosteroids, such as dexamethasone, are used as a prophylaxis for such infusion-related reactions in current intravenous docetaxel treatments. By using orally administered docetaxel, toxicity that may be associated with (long-term) treatment with corticosteroids may be avoided as well.

As used herein, the oral administration of docetaxel to a subject includes any route through the mouth of introducing or delivering to a subject the agent to perform its intended function. Suitable pharmaceutical compositions for oral administration includes liquids, tablets or capsules. Capsules and tablets may have an enteric coating, such that docetaxel is released from the capsules or tablets in the intestine. Capsules and tablets may be formulated in an extended release formulation such that docetaxel is released over an extended period, e.g., several hours or more, e.g., during the time spend in the intestinal tract. Tablets and capsules may thus be formulated such that the agent is released therefrom gradually. Tablets and capsules may be formulated such that the agent is released in the stomach or intestine. Tablets and capsules may be formulated such that the agent is released in the stomach and intestine. Administration includes self-administration and the administration by another.

Pharmaceutical compositions of this invention may comprise docetaxel, or pharmaceutically acceptable salts and esters thereof, and/or a CYP3A inhibitor, such as ritonavir, (or pharmaceutically acceptable salts and esters thereof) together with any pharmaceutically acceptable carrier, adjuvant or vehicle. Suitable preparations and/or pharmaceutical compositions for oral administrations include formulations as described in WO2009027644, WO2010020799 and Moes et al. Drug Deliv. Transl. Res. 2013) which are incorporated herein in its entirety by reference. Any suitable preparation for oral administration can be contemplated.

The current invention may not be restricted to oral administration of docetaxel. Any administration of docetaxel via the gastrointestinal tract may be contemplated. Hence, enteral administration can be contemplated herein instead of oral administration. Preferably, enteral administration is in the form of capsules, tablets, and suppositories. Docetaxel administration via a suppository may be advantageous, as bioavailability may be improved as compared with oral administration. This is because with oral administration, after passing the stomach and intestine, docetaxel is delivered to the liver via the portal vein. By enteral administration, the barriers that metabolize docetaxel in the first-pass may be avoided. Any enteral administration may suffice, as long as peak levels are avoided and effective plasma levels are obtained, as defined herein.

For many anticancer drugs such as docetaxel, cytochrome P450 represents a main oxidative drug metabolizing enzyme system. Cytochrome P450 (CYP) iso-enzymes, in particular CYP3A4, but also CYP3A5, are highly expressed in the liver and intestines. Intestinal extraction and metabolism of docetaxel by this enzyme system plays an important role in limiting oral bioavailability. As part of the metabolic route transporters also play a role. By the transport of compounds, such as docetaxel, in and out of the cell, the compound is provided as a substrate to the CYP3A4 and/or CYP3A5 enzymes. For example, the P-glycoprotein (P-gp, MDR1, ABCB1) plays a role in the metabolic route and transport of docetaxel. Hence, any compound that may have an effect on the metabolic route of docetaxel to thereby inhibit metabolizing docetaxel may be considered a suitable CYP3A inhibitor. Such compounds may e.g., have an effect on CYP3A4 and/or CYP3A5, and on P-glycoprotein (Er-jiaWang et al, Chem. Res. Toxicol. 2001; Wacher et al., Mol Carc. 1995), or may have distinct action on either CYP3A4 and/or CYP3A5, and on P-glycoprotein (Er-jiaWang et al, Chem. Res. Toxicol. 2001). Suitable CYP3A inhibitors may thus have an effect on both CYP3A4 (and CYP3A5) and P-glycoprotein. Suitable CYP3A inhibitors may thus have an effect on CYP3A4 and/or CYP3A5. Suitable CYP3A inhibitors may have an effect on P-glycoprotein. Hence, a CYP3A inhibitor is defined herein as a compound capable of reducing CYP3A4 and CYP3A5 metabolism in the cell. Said compound preferably is a pharmaceutical compound. Preferably, a CYP3A inhibitor is selected that inhibits CYP3A4, such as e.g., ritonavir. Ritonavir inhibits CYP3A5 and P-glycoprotein as well. Highly preferred is selective inhibition of CYP3A4.

In the methods of treatments of a cancer in a patient comprising orally administered docetaxel as described herein, preferably the plasma levels of docetaxel are at least partially controlled by administering a CYP3A inhibitor. The use of a CYP3A inhibitor accordingly assisting in transporting docetaxel from the stomach and/or intestine to the bloodstream, by reducing and/or inhibiting CYP3A4 and/or CYP3A5 activity in the cell. The use of a CYP3A inhibitor can thus provide for increased bioavailability of docetaxel. Such bioavailability may be increased, while not substantially increasing the peak levels of docetaxel. Hence, the use of a CYP3A inhibitor allows for the use of a lower dosage of oral docetaxel as effective plasma levels of docetaxel can be increased as compared with not using a CYP3A inhibitor. Alternatively, the use of a CYP3A inhibitor allows for the use of less frequent dosing of oral docetaxel, as effective plasma levels with the area under the curve as defined herein can be more efficiently obtained as compared with not using a CYP3A inhibitor.

Hence, in a method in accordance with the invention, the plasma levels of docetaxel are at least partially controlled by administering a CYP3A inhibitor. As said, the oral administration of docetaxel is to be combined with the use of a CYP3A inhibitor. Any CYP3A inhibitor may suffice, e.g., a suitable CYP3A inhibitor may be potent CYP3A inhibitors selected from the group consisting of boceprevir, claritromycine, erytromycine, indinavir, itraconazole, ketoconazole, posaconazole, ritonavir, saquinavir en voriconazole. Preferably a CYP3A inhibitor is used that has the least side effects. Most preferably, the CYP3A inhibitor that is combined with oral administration of docetaxel is ritonavir. Preferably, the CYP3A inhibitor for use in a combination therapy in accordance with the invention, comprises ritonavir administered in a dosage of 100 ng or 200 ng, or an equivalent dosage of another suitable CYP3A inhibitor. One can easily establish the suitable dosage for any other suitable inhibitor, as one can compare the effect of the CYP3A inhibitor ritonavir in a subject and select another CYP3A inhibitor and establish the dosage thereof that obtains the same effect. The effect being defined as the effect on docetaxel plasma levels (AUC) and/or peak plasma levels as obtained with the dosage of ritonavir used.

It is understood that in the methods and uses in accordance of the inventions, any additional use of compounds, including foods and further pharmaceuticals, that may have an impact on CYP3A activity, are preferably avoided as such foods may have an effect on the levels of docetaxel achieved in the plasma of subjects being treated. Hence, whichever potent CYP3A inhibitor is selected for the combined treatment with docetaxel, the further use of inhibitors of CYP3A by the subjects receiving treatment needs to be avoided as this may result in too high peak levels of docetaxel and/or too high area under the curves. Examples of further inhibitors that are preferably avoided are e.g., HIV Antivirals: indinavir, nelfinavir and saquinavir; Anti-microbial agents: clarithromycin, itraconazole, ketoconazole, nefazodone, telithromycin, erythromycin, fluconazole, chloramphenicol, ciprofloxacin, norfloxacin and voriconazole; Cardiac agents: verapamil, diltiazem, cimetidine and miodarone; other agents such as fluvoxamine; and also foods, such as star fruit and grapefruit juice. Conversely, preferably in the methods and uses of the invention, the use of compounds, including foods and further pharmaceuticals, that may induce CYP3A activity in the subjects receiving treatment, is preferably avoided as well, as such use may result in too high peak levels of docetaxel in plasma. Inducers of CYP3A that are preferably avoided are: HIV Antivirals: efavirenz and nevirapine; Other agents such as: barbiturates, carbamazepine, modafinil, nevirapine, oxcarbazepine, phenobarbital, phenytoin, pioglitazone, rifabutin, rifampicin and also St. John's wort.

In one embodiment, in the method in accordance with the invention said CYP3A inhibitor is simultaneously administered with docetaxel. It is understood that simultaneous administration can comprise separate administrations, e.g., in separate pharmaceutical preparations. For example, one pharmaceutical preparation suitable for oral administration comprising docetaxel and another pharmaceutical preparation comprising the CYP3A inhibitor, such as ritonavir. The pharmaceutical preparation comprising ritonavir preferably also being orally administered. It is understood that simultaneous administration can comprise one pharmaceutical preparation comprising both docetaxel and the CYP3A inhibitor, such as ritonavir. Docetaxel and the CYP3A inhibitor, can also be administered separately from each other. When they are administered separately, the CYP3A inhibitor is preferably administered before docetaxel, and, more preferably, within approximately 60 minutes before docetaxel is administered. Simultaneously, as used herein, means administration of the docetaxel or CYP3A inhibitor within e.g., approximately 20 minutes, more preferably within 15 minutes, more preferably within 10 minutes, even more preferably within 5 minutes, most preferably within 2 minutes of the CYP3A inhibitor or docetaxel. Generally, the CYP3A inhibitor is preferably orally administered simultaneously with administering oral docetaxel as this provides for optimal compliance in self-administration by subjects receiving treatment.

In another embodiment, in the methods in accordance with the invention said treatment of cancer comprises an extended use of more than 18 weeks. As said, the standard intravenous route of administration and standard use of docetaxel do not allow to recommend extended use because of the severe side effects and increasing toxicity associated with multiple administrations. Because of the improved methods of the invention, the methods of treatment now allow for a use that extends for longer periods. The methods of the invention allow for an extended use beyond 30 weeks, said methods comprising controlling or reducing the side effects associated with the use of docetaxel while maintaining an effective plasma level of docetaxel that eradicates tumor cells. Hence, in one embodiment, preferably, the methods of the invention allow for an extended use of at least 30 weeks of treatment. Such use allowing for an extended use of a year or more.

By knowing both the upper limits, i.e., peak plasma levels and/or range of effective plasma levels, the ranges within which docetaxel is to be administered in the methods and uses of the invention may allow for both effective tumor cell eradication and controlled or reduced side effects of docetaxel. The effective plasma level may be regarded to represent the range within which docetaxel can effectively eradicate cancer cells. The peak plasma levels may be regarded to represent the upper limit within which side effects of docetaxel can be controlled or reduced. Hence, any suitable pharmaceutical acceptable formulation and/or dosage regimen that operates within this range may be contemplated and is to provide the advantageous tumor cell eradication and side effect control or reduction of docetaxel as described herein and also allows for an extended use, as is not conceived as possible with the standard licensed treatments of intravenously administered docetaxel.

In the methods, or uses, in accordance with the invention, administrations of docetaxel can be on a tri-daily, bi-daily or daily basis, every two days, weekly, every two weeks, every three weeks or any other suitable dosing interval. Combinations of these dosage regimens can also be used, for example, the composition can be for bi-daily administration once every week or every two or three weeks. For example, docetaxel can be administered on a bi-daily basis once a week. The weekly dose is split so that a subject takes, for example, a first dose in the morning and the second dose in the evening once a week. This has the effect of decreasing the peak levels of the drug in plasma which may aid reducing side effects. It also may increase the time of systemic exposure of the drug. In a preferred embodiment, the methods, or uses, in accordance with the invention comprise docetaxel being administered weekly. Docetaxel may also be administered bidaily weekly, meaning that on one day every week, docetaxel is administered twice, e.g., within an 8-16 hours interval. As long as the dosing interval and/or dosage of docetaxel and the CYP3A inhibitor, such as ritonavir is selected that allows to provide preventing peak plasma levels thereby controlling or reducing side effects while maintaining effective plasma levels to eradicate tumor cells, such dosing interval and/or dosage may be contemplated.

In still a further embodiment, docetaxel is administered at a dosage of at least 10 mg per dosage administration, as such a dosage already can provide for effective plasma levels of docetaxel to eradicate tumor cells, while controlling or reducing side effects of docetaxel in patients. Preferably, said dosage is at least 20 mg per dosage administration. As said, docetaxel is administered preferably simultaneously with a CYP3A inhibitor, such as ritonavir. Preferably ritonavir is administered simultaneously at a dosage of at least 100 mg. Hence, in a method in accordance with the invention wherein ritonavir is simultaneously administered with docetaxel at each moment of dosing comprises the administration of 10 mg of docetaxel and 100 mg of ritonavir. Hence, in a further method in accordance with the invention, ritonavir is simultaneously administered with docetaxel at each moment of dosing comprising the administration at least 10 mg of docetaxel and at least 100 mg of ritonavir. As said, such an administration may be at a weekly schedule or a bidaily weekly schedule. Hence, a bidaily weekly schedule as described above at each moment of administration comprises the administration of at least 10 mg of docetaxel, or the administration of at least 10 mg of docetaxel and at least 100 mg of ritonavir. In another embodiment, a bidaily weekly schedule is provided for the treatment of cancer, wherein docetaxel is administered on one day a first administration at a dosage of 30 mg docetaxel with 100 mg ritonavir and a second administration at a dosage of 20 mg docetaxel with 100 mg ritonavir. In another embodiment, a bidaily weekly schedule is provided for the treatment of cancer, wherein docetaxel is administered on one day a first administration at a dosage of 30 mg docetaxel with 200 mg ritonavir and a second administration at a dosage of 20 mg docetaxel with 100 mg ritonavir. In another embodiment, a bidaily weekly schedule is provided for the treatment of cancer, wherein docetaxel is administered on one day a first administration at a dosage of 30 mg docetaxel with 200 mg ritonavir and a second administration at a dosage of 20 mg docetaxel with 200 mg ritonavir.

In another embodiment, a bidaily weekly schedule is provided for the treatment of cancer, wherein docetaxel is administered on one day a first administration at a dosage of 20 mg docetaxel with 200 mg ritonavir and a second administration at a dosage of 20 mg docetaxel with 200 mg ritonavir. In another embodiment, a bidaily weekly schedule is provided for the treatment of cancer, wherein docetaxel is administered on one day a first administration at a dosage of 20 mg docetaxel with 100 mg ritonavir and a second administration at a dosage of 20 mg docetaxel with 100 mg ritonavir. In another embodiment, a bidaily weekly schedule is provided for the treatment of cancer, wherein docetaxel is administered on one day a first administration at a dosage of 20 mg docetaxel with 200 mg ritonavir and a second administration at a dosage of 20 mg docetaxel with 100 mg ritonavir.

In another embodiment, in a method in accordance with the invention the cancer is a solid tumor. In methods in accordance with the invention, the cancer being treated may be the same as currently prescribed for intravenous administrations of docetaxel. Hence, preferably, the methods include treatments of cancer wherein the cancer is a solid tumor selected from the group consisting of gastric cancer, breast cancer, head and neck cancer, lung cancer and prostate cancer.

In one embodiment, the current invention provides for a combination of a CYP3A inhibitor and docetaxel for use in a medical treatment of a cancer, wherein said use comprises oral administration of docetaxel, said use comprises preventing peak plasma levels of docetaxel that induce side effects whilst maintaining plasma levels of docetaxel that eradicate tumor cells. In another embodiment, the current invention provides for docetaxel for use in a combination therapy in the treatment of cancer, wherein said docetaxel is to be administered in combination with a CYP3A inhibitor and wherein said use comprises oral administration of docetaxel, and wherein said use comprises preventing peak plasma levels of docetaxel that induce side effects whilst maintaining plasma levels of docetaxel that eradicate tumor cells. In still another embodiment, the invention provides for a CYP3A inhibitor for use in a combination therapy in the treatment of cancer, wherein said CYP3A inhibitor is to be administered in combination with docetaxel and wherein docetaxel is administered orally, said use comprising preventing peak plasma levels of docetaxel that induce side effects whilst maintaining plasma levels of docetaxel that eradicate tumor cells. Said CYP3A inhibitor in these embodiments is preferably ritonavir.

Similar to as described herein for the methods of the invention, said uses as described above comprises peak plasma levels of docetaxel of at most 2500 ng/mL. Said upper limit provides plasma levels that are not associated with side effects. Said uses as described above preferably comprise effective plasma levels of docetaxel in the range of an AUC in between 800 and 2000 ngh/mL. Likewise, said uses as described above preferably comprise effective plasma levels of docetaxel in the range of an AUC in between 1000 and 2000 ngh/mL. Said uses preferably comprise an extended use of more than 30 weeks. Said uses preferably comprise the treatments of cancer wherein the cancer is a solid tumor. Said uses preferably comprise a cancer wherein the cancer is a solid tumor selected from the group consisting of gastric cancer, breast cancer, head and neck cancer, lung cancer and prostate cancer.

The current invention also provides for a kit comprising a pharmaceutical composition for oral administration comprising docetaxel and a pharmaceutical composition comprising a CYP3A inhibitor, wherein said kit is for extended use in the treatment of cancer. Furthermore, a kit is provided comprising a pharmaceutical composition for oral administration comprising docetaxel and a pharmaceutical composition comprising a CYP3A inhibitor, wherein said kit is for uses and methods as described herein.

As used in the description of the invention, clauses and appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

EXAMPLES

Modradoc006

Modradoc006 is a spray-dried solid dispersion formulation of docetaxel pressed into tablets (ModraDoc006 10 mg tablets), containing 10 mg docetaxel. The formulation excipients are polyvinyl pyrrolidone K30, sodium dodecyl sulphate, lactose monohydrate, croscarmellose, silica colloidalis anhydrica and magnesium stearate. All excipients are included in the FDA guide for inactive compounds (oral capsules and tablets).

Ritonavir

Ritonavir is commercially available as 100 mg tablets for oral consumption (Norvir®). This tablet has been granted approval by the European Commission in 2010.

Docetaxel and Ritonavir Plasma Measurements

A combined assay for the determination of docetaxel and ritonavir in human plasma is described. The drugs were extracted from 200 μL human plasma using liquid-liquid extraction with tertiary-butylmethylether, followed by high performance liquid chromatography analysis using 10 mM ammonium hydroxide pH 10:methanol (3:7, v/v) as mobile phase. Chromatographic separation was obtained using a Zorbax Extend C(18) column. Labelled analogues of the analytes are used as internal standards. For detection, positive ionization electrospray tandem mass spectrometry was used. Method development including optimisation of the mass transitions and response, mobile phase optimisation and column selection are discussed. The method was validated according to FDA guidelines and the principles of Good Laboratory Practice (GLP). The validated range was 0.5-500 ng/mL for docetaxel and 2-2000 ng/mL for ritonavir. For quantification, quadratic calibration curves were used ($r(2)>0.99$). The total runtime of the method is 9 min and the assay combines analytes with differences in ionisation and desired concentration range. Inter-assay accuracy and precision were tested at four concentration levels and were within 10% and less than 10%, respectively, for all analytes. Carry-over was less than 6% and endogenous interferences or interferences between analytes and internal standards were less than 20% of the response at the lower limit of quantification level. The matrix factor and recovery were determined at low, mid and high concentration levels. The matrix factor was around 1 for all analytes and total recovery between 77.5 and 104%. Stability was investigated in stock solutions, human plasma, dry extracts, final extracts and during 3 freeze/thaw cycles. The described method was successfully applied in clinical studies with oral administration of docetaxel in combination with ritonavir.

Extended Use

N07DOW

We treated in a phase I trial (N07DOW) cancer patients (n=100) with oral docetaxel in combination with ritonavir. The dose was administered on one day (single dose), once per week. Data presented as mean±standard deviation. If available, kinetic data of 2 cycles per patient were used.

Treatment duration of 19 patients was from 19 up to 72 weeks. These were patients with the following cancers. Head and neck (n=1), non-small cell lung (n=8), anal (n=1), primary unknown (n=3), ovarian (n=1), esophageal (n=1), urothelial cell (n=2), leiomyosarcoma (n=1) and neuroendocrine lung carcinoma (n=1). The docetaxel exposure in these patients was:
AUC0-48h 803±634 h·ng/mL
CMAX (peak) 148±113 ng/mL SAEs (Serious adverse events) and DLTs (Dose-Limiting Toxicity) (possible, probable, definite; ≥grade 3) were noted in 15 patients. The docetaxel exposure in these patients was:
AUC0-48h 2345±1453 h·ng/mL
CMAX 351±244 ng/mL Fiftytwo patients had SD (stable disease) (n=42) or PR (partial response) (n=10) as best treatment response. The docetaxel exposure in these patients was:
AUC0-48h 1083±1023 h·ng/mL
CMAX 197±186 ng/mL

N10BOM

We treated in a phase I trial (N10BOM) cancer patients (n=64) with oral docetaxel in combination with ritonavir. The dose was administered bi-daily once per week continuously.

Treatment duration of 8 patients was from 19 up to 55 weeks. These were patients with the following cancers. Head and neck cancer (n=2; PR), non-small cell lung (n=4; SD), colorectal (n=1;SD) and giant cell neuroendocrine carcinoma (n=1;SD). The docetaxel exposure in these patients was:
AUC0-48h 1224±620 h·ng/mL
CMAX 143±67 ng/mL SAEs and DLTs (possible, probable, definite; ≥grade 3) were noted in 10 patients. The docetaxel exposure in these patients was:
AUC0-48h 1809±1255 h·ng/mL
CMAX 175±117 ng/mL Twentyfive patients had SD or PR as best treatment response. The docetaxel exposure in these patients was:
AUC0-48h 1242±702 h·ng/mL
CMAX 140±83 ng/mL To Summarize Treatment duration 19 weeks and longer:

|  | N07DOW | N10BOM |
| --- | --- | --- |
| AUC0-48 h | 803 ± 634 h · ng/mL | 1224 ± 620 h · ng/mL |
| CMAX | 148 ± 113 ng/mL | 143 ± 67 ng/mL |

SAEs and DLTs

|  | N07DOW | N10BOM |
| --- | --- | --- |
| AUC0-48 h | 2345 ± 1453 h · ng/mL | 1809 ± 1255 h · ng/mL |
| CMAX | 351 ± 244 ng/mL | 175 ± 117 ng/mL |

SDs and PRs responses

|  | N07DOW | N10BOM |
| --- | --- | --- |
| AUC0-48 h | 1083 ± 1023 h · ng/mL | 1242 ± 702 h · ng/mL |
| CMAX | 197 ± 186 ng/mL | 140 ± 83 ng/mL |

For Comparison:

A weekly administration of docetaxel (35 mg/m2) as a 0.5 h intravenous infusion gives the following AUC and CMAX-values.
AUC 1480±410 h·ng/mL
CMAX 1930±600 ng/mL Baker SD et al. Clin Cancer Res 2004; 10:1976-1983.

For bi-daily, once per week use of oral docetaxel with ritonavir (ModraDoc006/r) the following targeted values may be proposed:
AUC 1200±600 h·ng/mL
CMAX 140±70 ng/mL With this weekly oral treatment schedule similar docetaxel exposure (AUC) is achieved on the administration day, as on the administration day of the weekly intravenous treatment schedule (moreover, intravenously often given as 3 consecutive weeks followed with 1 week rest while oral docetaxel is given continuously with no rest week). CMAX values after this intravenous administration (35 mg/m2 in 0.5 h) are ten-fold higher than after oral ModraDoc006/r 30-20/100-100 in patients with solid tumors (not prostate).

Intravenous (35 mg/m2) docetaxel and oral docetaxel treatment (ModraDoc006/r 30-20/100-100) give similar AUCs and thus comparable efficacy is to be expected;

Intravenous (35 mg/m2 in 0.5 h) docetaxel gives a tenfold higher CMAX than oral docetaxel treatment (ModraDoc006/r 30-20/100-100) which may explain higher toxicity for the intravenous treatment;

In oral docetaxel treatment (ModraDoc006/r) higher AUC0-48h-CMAX values correlate with toxicity;

For oral docetaxel treatment (ModraDoc006/r) an AUC0-48h of 1200±600 h·ng/mL seems optimal and which can be achieved in cancer patients with solid tumors (not prostate) by a bi-daily weekly schedule with ModraDoc006/r 30-20/100-100.

mCRPC Trial

In a phase I trial we investigated oral treatment with ModraDoc006/r in patients with several solid tumors (not prostate). From this study it was concluded that the recommended dose for phase II efficacy evaluation is:

ModraDoc006 30 mg+Ritonavir 100 mg, taken simultaneously in the morning

ModraDoc006 20 mg+Ritonavir 100 mg, taken simultaneously in the evening

This treatment (denoted as ModraDoc006/r 30-20/100-100) is given on one day, once every week.

Pharmacokinetics research revealed that the docetaxel AUC0-48h of this treatment schedule of cycle 1 is: 1126±382 h·ng/mL. The CMAX value was 102±46 ng/mL (average of 16 treated patients).

Our next step was to investigate this oral treatment schedule in patients with metastatic Castration Resistant Prostate Cancer (mCRPC) in a phaseIB/.IIA trial. Surprisingly, in the first 5 patients treated with the recommended dose from the phase I trial (ModraDoc006/r 30-20/100-100), we noted a much lower docetaxel exposure (AUC0-48h) of 498±298 h·ng/mL, approximately half than expected. The CMAX values: 45±31 ng/mL, were also half than expected. Patients experienced no notable side effects. It was concluded that docetaxel has a higher clearance in this mCRPC patient population than in patients with other solid tumors.

We then hypothesized that we could achieve our targeted exposure of around 1100±500 h·ng/mL by increasing (doubling) the CYP3A inhibitor ritonavir dose. Eight mCRPC patients were then treated with ModraDoc006/r 30-20/200-200 (taken on one day, once per week). The docetaxel exposure in this cohort was: AUC0-48h 2032±1018 h·ng/mL and CMAX 164±80 ng/mL. These values were higher than expected. Patients also experienced more side effects (grade III).

Next, we treated mCRPC patients (n=3) with the dose ModraDoc006/r 30-20/200-100 in the assumption that with a reduced ritonavir dose the docetaxel exposure would decrease towards its targeted value. In this treated cohort of patients, the docetaxel exposure was AUC from 0-48h 1130±257 h·ng/mL and CMAX 135±46 ng/mL. Treatment is well tolerated.

Figure 1:
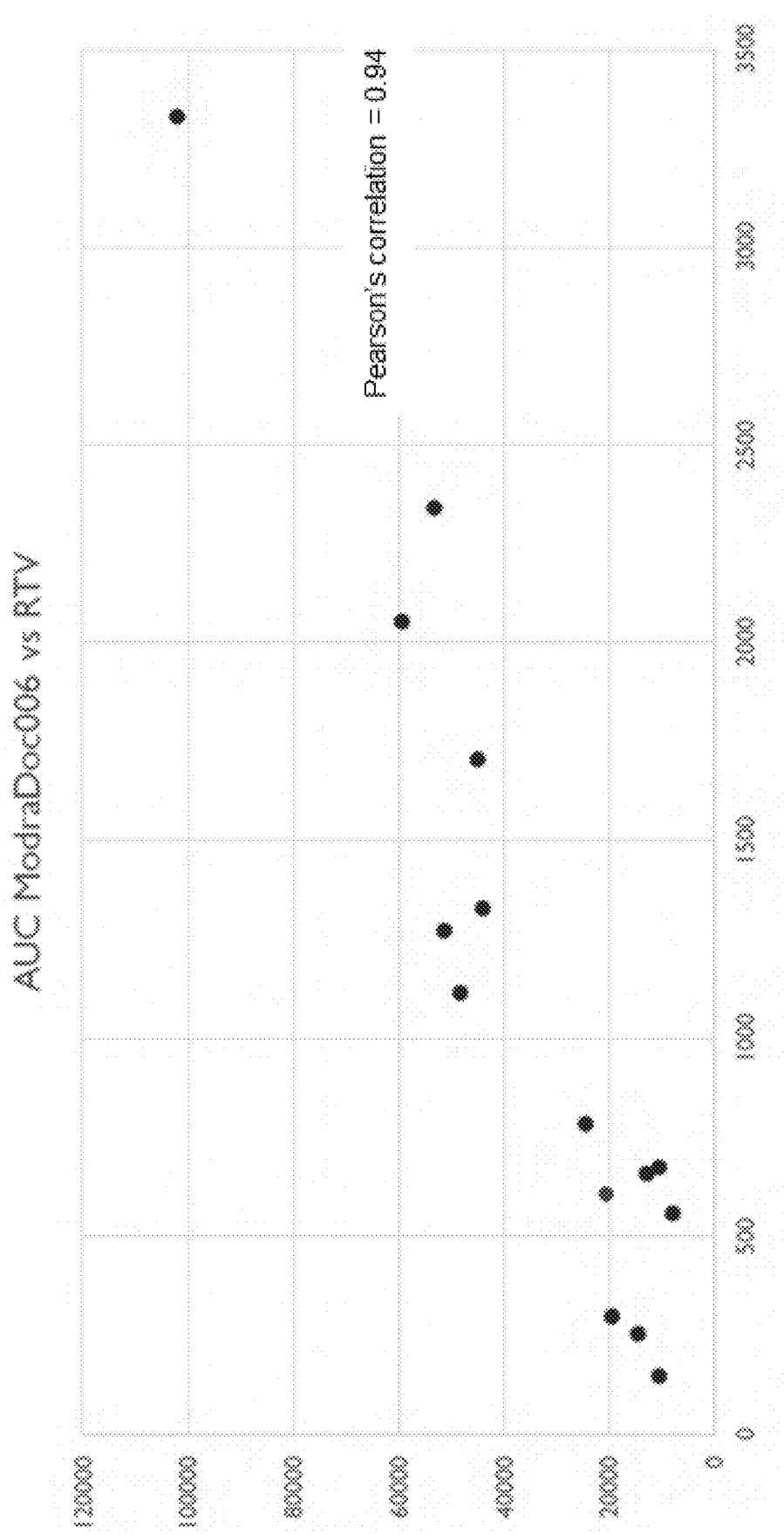
In FIG. 1 a plot is shown presenting AUC (average AUCs in h*ng/mL by dose level) of ritonavir (RTV) to ModraDoc006 (docetaxel). It shows that exposure of Modrodoc006 appears to be highly correlated to overall Ritonavir AUC (and dose).
Figure 2A:
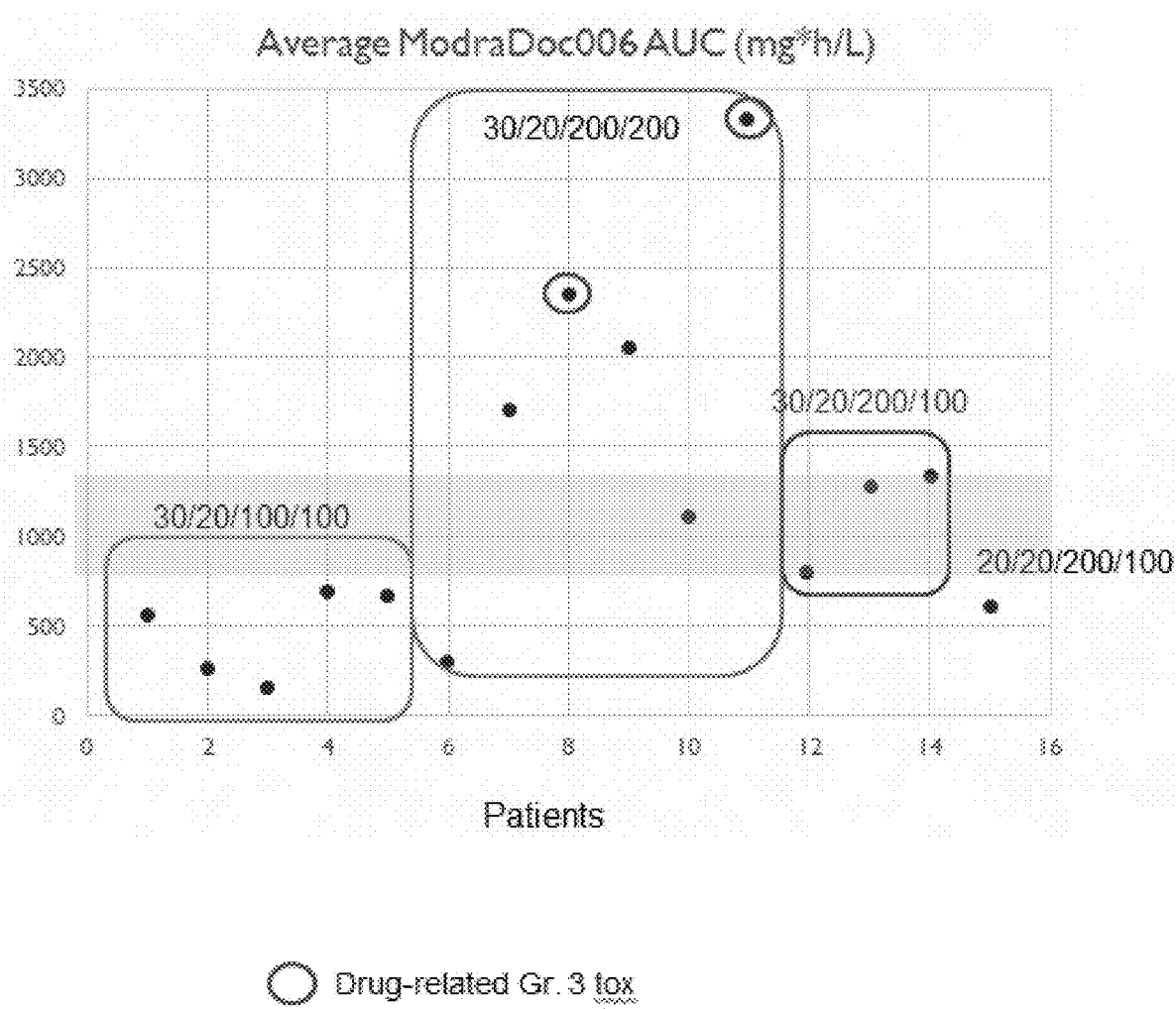
In FIG. 2A a plot is shown indicating similar or moderately higher levels of docetaxel AUC are obtained in patients as compared with IV.
Figure 2B:
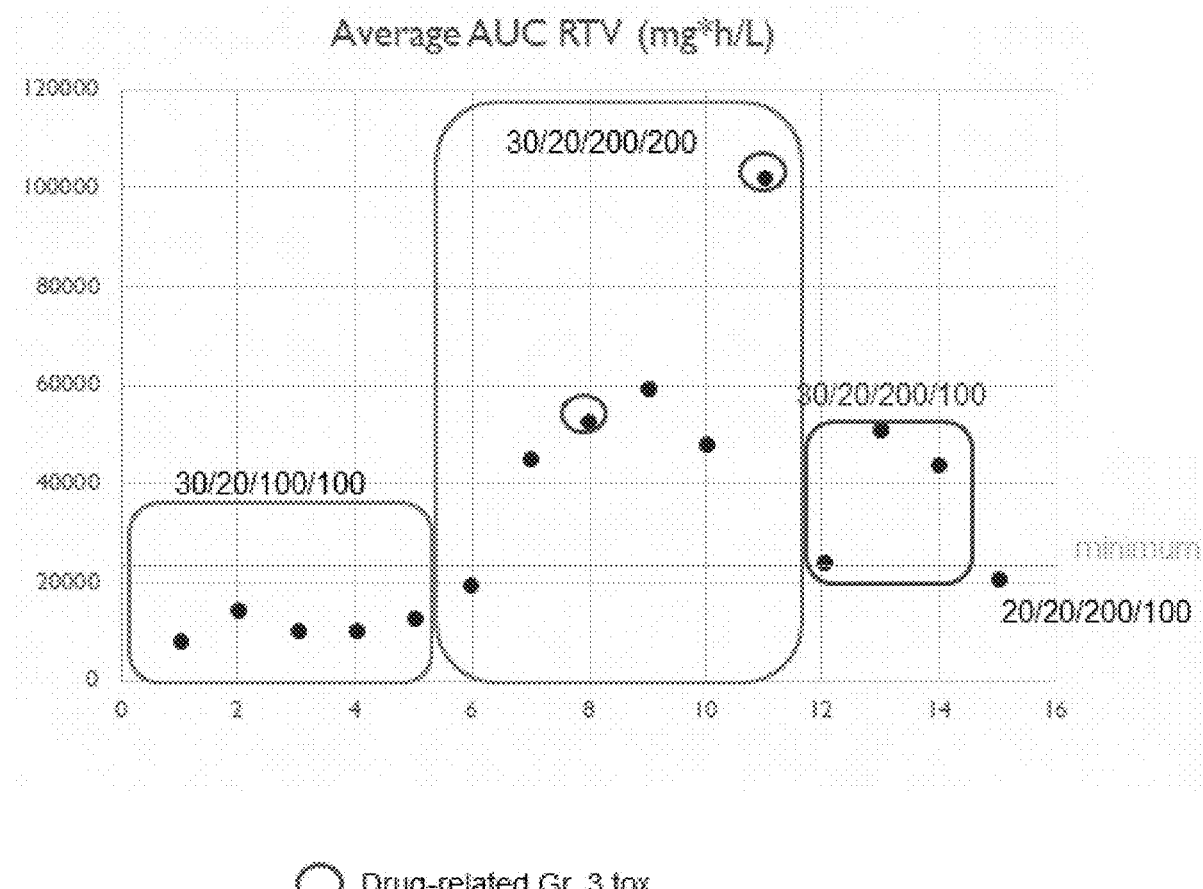
In FIG. 2B a plot is shown with the AUC of ritonavir.
Figure 3:
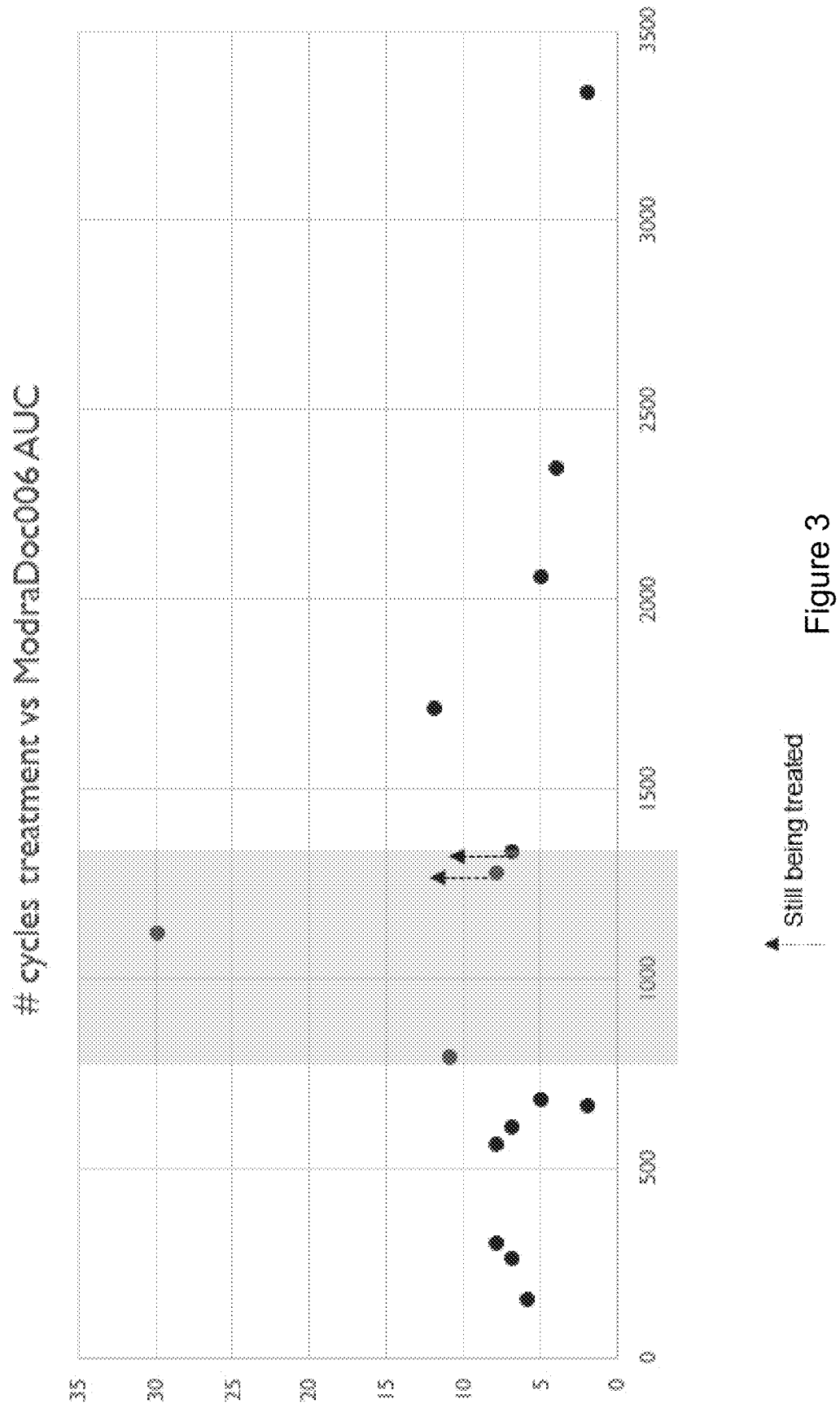
In FIG. 3 a plot is shown of docetaxel AUC and number of cycles. Length of treatment appears to be trending longer in patients in a target docetaxel range.
Figure 4:
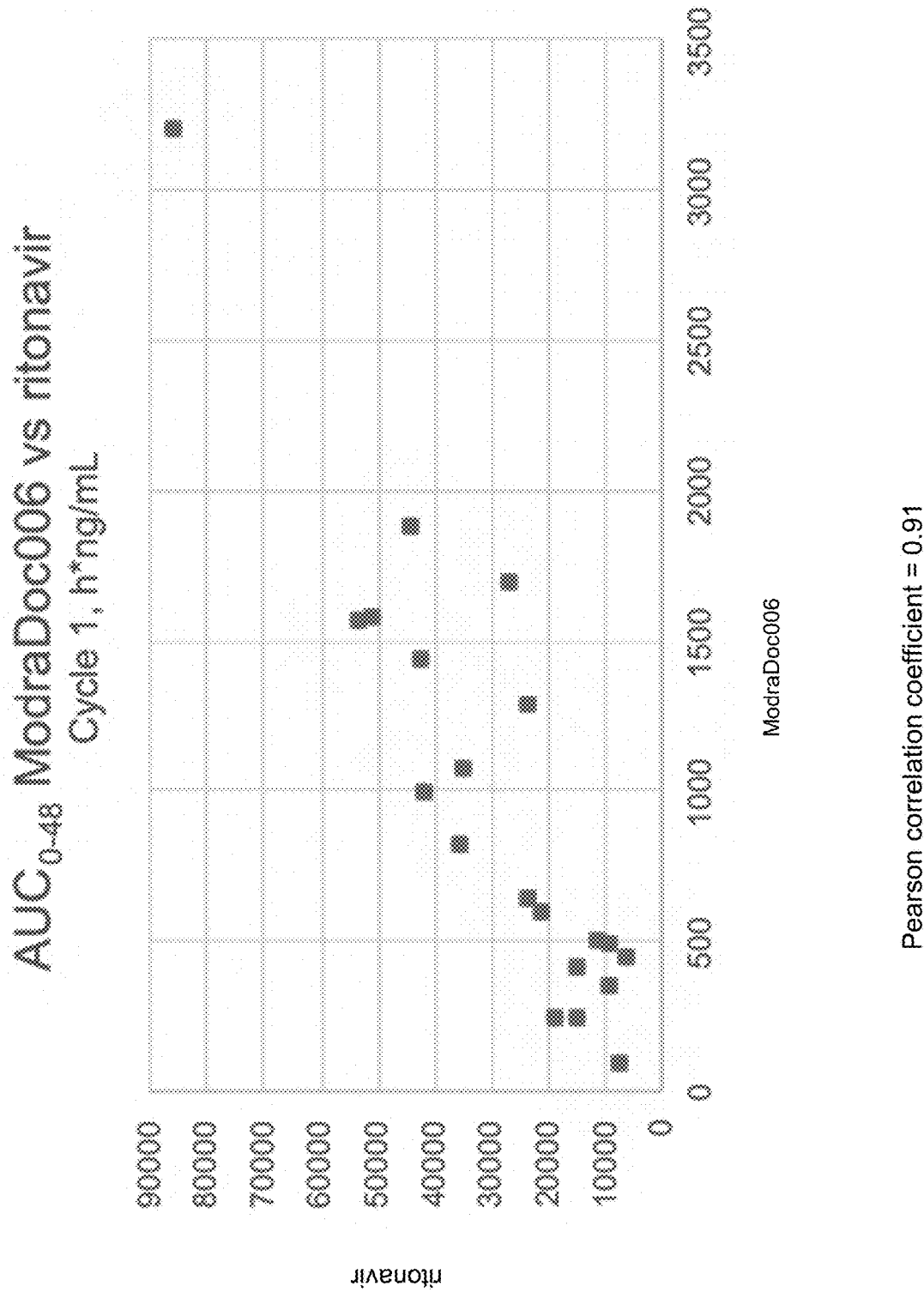
FIGS. 4, 5A, 5B and 6 represent updates of FIGS. 1, 2A, 2B, and 3, respectively.

Results are also depicted in FIGS. 2A and 2B.

To Summarize:

| ModraDoc006/r | docetaxel AUC0-48 h (h · ng/mL) | docetaxel CMAX (ng/mL) |
|---|---|---|
| 30-20/100-100 (phase I →target) | 1100 | 100 |
| 30-20/100-100 (phase IB/IIA mCRPC) | 500 | 45 |
| 30-20/200-200 (phase IB/IIA mCRPC) | 2000 | 165 |
| 30-20/200-100 (phase IB/IIA mCRPC) | 1100 | 135 |

Data rounded off and with variation that may occur up to 40-50%.

The trial results described above were obtained during the trial and represent intermediate results. The trial continued and below updated results are described.

Phase IB/IIA Study in mCRPC

A multicenter clinical phase IB/IIA study was conducted in mCRPC (M17DOC), wherein ModraDoc006, an oral docetaxel formulation was combined with ritonavir (ModraDoc006/r), in metastasized castration-resistant prostate cancer (mCRPC).

The study included patients diagnosed with metastasized castration-resistant prostate cancer (mCRPC), dosed in a bi-daily once weekly (BIDW) dosing schedule at 4 dose levels (see table below).

| Dose level | ModraDoc006 | Ritonavir | # patients |
|---|---|---|---|
| −2A | 30 mg/20 mg | 100 mg/100 mg | 5 |
| 1A | 30 mg/20 mg | 200 mg/200 mg | 6 |
| −1A | 30 mg/20 mg | 200 mg/100 mg | 6 |
| −2B | 20 mg/20 mg | 200 mg/100 mg | 3 |

As said, surprisingly, in the first 5 patients treated with the recommended dose from the phase I trial (ModraDoc006/r 30-20/100-100), a much lower docetaxel exposure in cycle 1 (median AUC0-48h±SD) of 454±181 h·ng/mL, approximately half than expected. The CMAX values: 38±18 ng/mL, were also half than expected. Patients experienced no notable side effects. It was concluded that docetaxel has a higher clearance in this mCRPC patient population than in patients with other solid tumors.

As said, we then hypothesized that we could achieve our targeted exposure of around 1100±500 h·ng/mL by increasing (doubling) the CYP3A inhibitor ritonavir dose. Eight patients mCRPC, of which six were evaluable, were then treated with ModraDoc006/r 30-20/200-200 (taken on one day, once per week). The docetaxel exposure in this cohort in cycle 1 was: median AUC0-48h±SD 1510±990 h·ng/mL and CMAX 146±82 ng/mL. These values were higher than expected. Patients also experienced more side effects (grade III).

Next we treated mCRPC patients (n=6) with the dose ModraDoc006/r 30-20/200-100 in the assumption that with a reduced ritonavir dose the docetaxel exposure would decrease towards its targeted value. In this treated cohort of patients the docetaxel exposure was in cycle 1: median AUC from 0-48h±SD 1189±473 h·ng/mL and CMAX 159±49 ng/mL. Treatment is well tolerated.

In mCRPC patients (n=3) treated with ModraDoc006/r 20-20/200-100, with thus a reduced docetaxel morning dose, the docetaxel exposure was in cycle 1: median AUC from 0-48h ±SD 419±158 h·ng/mL and CMAX 53±21 ng/mL.

To Summarize:

| ModraDoc006/r | docetaxel AUC0-48 h (h · ng/mL) | docetaxel CMAX (ng/mL) |
|---|---|---|
| 30-20/100-100 (prior phase I →target) | 1100 | 100 |
| 30-20/100-100 (phase IB/IIA mCRPC) | 500 | 40 |
| 30-20/200-200 (phase IB/IIA mCRPC) | 1500 | 150 |
| 30-20/200-100 (phase IB/IIA mCRPC) | 1200 | 160 |
| 20-20/200-100 (phase IB/IIA mCRPC) | 420 | 50 |

Median values for cycle 1 are rounded off and with variation that may occur up to 40-50%.

Results of the trial are further listed below and depicted in FIGS. 4 to 8.

| Patient # | total # cycles | PSA Change % | Best PSA response | Radiological response |
|---|---|---|---|---|
| | | | Dose level −2A | |
| #0101 | 8 | −11% | PSA equal to baseline or decline <50% | non CR/non PD |
| #0102 | 7 | 19% | PSA increase | SD |
| #0103 | 6 | 144% | PSA increase | non CR/non PD |
| #0104 | 5 | −6% | PSA equal to baseline or decline <50% | — |
| #0105 | 2 | −11% | PSA equal to baseline or decline <50% | — |
| | | | Dose level 1A | |
| #0301 (NE) | 1 | −17% | PSA equal to baseline or decline <50% | NE |
| #0106 | 8 | 44% | PSA increase, suspected progression | non CR/non PD |
| #0302 | 12 | −53% | PSA response, non-confirmed | SD |
| #0201 (NE) | 2 | −10% | PSA equal to baseline or decline <50% | NE |
| #0401 (DLT) | 4 | −40% | PSA equal to baseline or decline <50% | — |
| #0303 | 5 | 84% | PSA increase, suspected flare-up | SD (after 5 cycles) |
| #0402 | 30 | −98% | PSA response, confirmed | non CR/non PD |
| #0202 (DLT) | 3 | −70% | PSA response, confirmed | SD (after 3 cycles) |
| | | | Dose level −1A | |
| #0304 | 11 | 14% | PSA equal to baseline or decline <50% | PD |
| #0403 | 17 | −33% | PSA equal to baseline or decline <50% | non CR/non PD |
| #0404 | 30 | 61% | PSA increase, suspected flare-up | non CR/non PD |
| #0109 (NE) | 2 | −31% | PSA equal to baseline or decline <50% | NE |
| #0306 | 12 | −60% | PSA response, non-confirmed | SD |
| #0307 (DLT) | 3 | 0% | PSA equal to baseline or decline <50% | — |
| #0406 | 27 | −95% | PSA response, confirmed | non CR/non PD |
| | | | Dose level −2B | |
| #0107 | 30 | −97% | PSA response, confirmed | PR |
| #0305 (NE) | 0 | | | NE |
| #0108 | 30 | −34% | PSA equal to baseline or decline <50% | non CR/non PD |
| #0405 | 30 | −91% | PSA response, confirmed | PR |

(PSA (prostate specific antigen); SD (Stable disease); non CR(non complete response); non PD (non-progressive disease); PD (progressive disease); NE (non evaluable); PR (partial response)). Efficacy summary:

This study included 20 evaluable patients diagnosed with metastasized castration-resistant prostate cancer (mCRPC), dosed in a bi-daily once weekly (BIDW) dosing schedule at 4 dose levels (see table). In 7 patients PSA response (PSA decline ≥50%) was observed, of which 5 were confirmed by a second measurement after 6 weeks. In another 7 patients PSA declined <50% or remained equal to baseline. In the remaining 6 patients PSA increase was observed. Despite PSA decline <50% in one patient and PSA increase in another patient, noticeable clinical response with pain reduction was achieved during the maximum treatment duration of 30 weeks. A total of 5 patients completed the maximum of 30 treatment weeks. The median treatment duration was 14 weeks. ModraDoc006/r 30-20/200-100 is a preferred initial dose to be further tested in mCRPC, given it demonstrated the ability to achieve exposure levels of docetaxel (as measured by AUC) which were higher than achieved with IV docetaxel, while also having acceptable toxicity. Alternatively ModraDoc006/r 20-20/200-100 may be another preferred dose, or preferred initial dose, in mCRPC.

Phase IIA Study in Breast Cancer

A multicenter clinical phase IIA study was conducted in metastatic breast cancer (M18DMB), wherein ModraDoc006, an oral docetaxel formulation was combined with ritonavir (ModraDoc006/r), in patients with recurrent or metastatic HER-2 negative breast cancer suitable for treatment with a taxane. Results of the trial are summarized below and depicted in FIGS. 9 and 10.

| Patient # | Tumor measurements (mm) | Total # of cycles | Best response (%) | Overall Response |
|---|---|---|---|---|
| 001 | 58-48.4 | 8 | −17% | PD |
| 002 | 16 | 2 | | NE |
| 003 | 22.6-15.2-12.3 | 12 | −46% | PR-c |
| 004 | 49-51-53-59 | 78 | 4% | SD |
| 005 | 47-48-55 | 12 | 2% | SD |
| 006 | 68-60-51 | 12 | −25% | SD |
| 007 | — | | | — |
| 008 | 22-22 | 6 | 0% | SD |
| 009 | 37-28 | 6 | −24% | SD |
| 010 | 79-64-35 | 22 ong | −66% | PR-c |
| 011 | 68-47 | 20 ong | −38% | PR-c |
| 012 | 29 | 7 | | NE |
| 013 | 77-73-63 | 12 | −18% | SD |

(PD (progressive disease); NE (Non-evaluable); PR-c (confirmed Partial Response), ong (ongoing).
Tumor measurements represent changes in tumor size over time as measured by CT scan, with the initial value being baseline.

Efficacy Summary:

A total of 12 patients with recurrent or metastatic breast cancer, suitable for treatment with a taxane, were treated in this study at a bi-daily once weekly (BIDW) dosing schedule with thirty (30) mg ModraDoc006 combined with 100 mg ritonavir (/r) in the morning and 20 mg ModraDoc006 with 100 mg/r in evening. In 10 patients evaluable for efficacy (i.e., they received a minimum of 6 weekly treatments and with disease assessments according to RECIST 1.1.), responses resulted in 3 confirmed (repeated tumor measurement after >4 weeks) partial responses (PR), 6 stable disease (SD) and 1 progressive disease (PD). Median treatment duration in 12 patients is currently 11.3 weeks, with 2 patients still ongoing at respectively 20 and 22 weeks.

The invention claimed is:

1. A method, comprising:
   orally administering a series of therapeutically-effective weekly doses of docetaxel, or pharmaceutically acceptable salt or ester thereof, to a patient having a solid cancerous tumor, for a period of more than 18 weeks, thereby eradicating cells of the solid tumor, wherein the weekly doses are sufficient to produce an effective plasma level of at least 400 ng·h/mL docetaxel in the patient plasma;
   maintaining a peak plasma level of at most 2500 ng/mL docetaxel in the patient plasma, thereby reducing docetaxel-induced neutropenia in the patient; and
   administering a CYP3A inhibitor to the patient with each dose in the series of therapeutically-effective weekly doses.

2. The method of claim 1, wherein the effective plasma level is defined as the area under a plasma docetaxel concentration-time curve (AUC) as determined in the first 48 hours after administration of each weekly dose of docetaxel, or pharmaceutically acceptable salt or ester thereof.

3. The method of claim 1, wherein each weekly dose comprises at least 20 mg docetaxel, or pharmaceutically acceptable salt or ester thereof.

4. The method of claim 1, wherein each weekly dose comprises a bidaily weekly dose, comprising two doses of docetaxel, or pharmaceutically acceptable salt or ester thereof, the two doses comprising a first dose of docetaxel, or pharmaceutically acceptable salt or ester thereof, and a second dose of docetaxel, or pharmaceutically acceptable salt or ester thereof, administered in the same day or 24-hour period.

5. The method of claim 4, wherein each of the two doses comprises at least 10 mg docetaxel, or pharmaceutically acceptable salt or ester thereof.

6. The method of claim 4, wherein the effective plasma level is defined as the area under a plasma docetaxel concentration-time curve (AUC) as determined in the first 48 hours after administration of the second dose of docetaxel, or pharmaceutically acceptable salt or ester thereof.

7. The method of claim 1, wherein each weekly dose in the series of therapeutically-effective weekly doses is sufficient to produce an effective plasma level of: at least 500 ng·h/mL docetaxel in the patient plasma; or between 500 ng·h/mL and 1500 ng·h/mL docetaxel in the patient plasma.

8. The method of claim 1 further comprising maintaining a peak plasma level of at most 500 ng/mL docetaxel in the patient plasma.

9. The method of claim 1, wherein the series of therapeutically-effective weekly doses of docetaxel, or pharmaceutically acceptable salt or ester thereof, is administered for a period of at least 30 weeks.

10. The method of claim 1, wherein the CYP3A inhibitor is administered to the patient simultaneously with each individual dose of docetaxel, or pharmaceutically acceptable salt or ester thereof, in the series of therapeutically-effective weekly doses.

11. The method of claim 1, wherein the CYP3A inhibitor comprises ritonavir.

12. The method of claim 11, wherein the ritonavir is administered at a dosage of at least 100 mg per dose.

13. A method, comprising:
   orally administering a series of therapeutically-effective weekly doses of docetaxel, or pharmaceutically acceptable salt or ester thereof, to a patient having a solid cancerous tumor, for a period of more than 30 weeks, thereby eradicating cells of the solid tumor, wherein:
      each of the weekly doses comprises at least 20 mg docetaxel, or pharmaceutically acceptable salt or ester thereof, and is sufficient to produce an effective plasma level of at least 400 ng·h/mL docetaxel in the patient plasma, and wherein the effective plasma level is defined as the area under a plasma docetaxel concentration-time curve (AUC) as determined in the first 48 hours after administration of each of the weekly doses of docetaxel, or pharmaceutically acceptable salt or ester thereof, or
      each of the weekly doses comprises a bidaily weekly dose, comprising two doses of docetaxel, or pharmaceutically acceptable salt or ester thereof, the two doses comprising a first dose of docetaxel, or pharmaceutically acceptable salt or ester thereof, and a second dose of docetaxel, or pharmaceutically acceptable salt or ester thereof, administered in the same 8-16 hour period, wherein each of the two doses comprises at least 10 mg docetaxel, or pharmaceutically acceptable salt or ester thereof, and wherein the effective plasma level is defined as the area under a plasma docetaxel concentration-time curve (AUC) as determined in the first 48 hours after administration of the second dose of docetaxel, or pharmaceutically acceptable salt or ester thereof;
   maintaining a peak plasma level of at most 500 ng/mL docetaxel in the patient plasma, thereby reducing docetaxel-induced neutropenia in the patient; and
   administering at least 100 mg of ritonavir to the patient with each individual dose of docetaxel, or pharmaceutically acceptable salt or ester thereof, in the series of therapeutically-effective weekly doses.

* * * * *